United States Patent [19]

Freed et al.

[11] 4,076,953

[45] Feb. 28, 1978

[54] 1,3-BRIDGED AMINO TETRALINS

[75] Inventors: Meier E. Freed, Paoli; John R. Potoski, Spring City, both of Pa.

[73] Assignee: American Home Products Corporation, New York, N.Y.

[21] Appl. No.: 769,605

[22] Filed: Feb. 17, 1977

Related U.S. Application Data

[62] Division of Ser. No. 558,021, Mar. 13, 1975, Pat. No. 4,034,041.

[51] Int. Cl.$^2$ .................. C07C 69/00; C07C 79/46

[52] U.S. Cl. .................. 560/142; 260/566 A; 260/566 AE; 260/571; 424/309; 424/311; 424/316; 424/330; 560/101

[58] Field of Search ............ 260/471 A, 479 R, 571

[56] References Cited

U.S. PATENT DOCUMENTS 4,034,041  7/1977  Freed et al. .................. 260/571

*Primary Examiner*—Robert V. Hines
*Attorney, Agent, or Firm*—Robert Wiser

[57] ABSTRACT

1,3-Bridged-2-amino tetralins, having spiro substitution or the bridge, and intermediates thereto. The final products have analgesic activity.

2 Claims, No Drawings

1,3-BRIDGED AMINO TETRALINS

This is a division of application Ser. No. 558,021, filed Mar. 13, 1975, and now U.S. Pat. No. 4,034,041.

BACKGROUND OF THE INVENTION

U.S. Pat. No. 3,836,670 relates to, inter alia, 5,6,7,8,9,10-hexahydro-3-substituted-5-substituted-5,9-methanobenzocycloocten-11-amines, and 5,6,7,8,9,10,11,12-octahydro-3-substituted-5-substituted-5, 11-methanobenzocyclodecen-13-amines. This application relates to compounds having a similar parent ring structure, but which have alkyl substituents introduced in a spiro arrangement on the macrocyclic ring. These substituents are located in a position whereby they may be expected to have a significant influence on the relative spatial position of the carbocyclic ring systems and the amino substituent relative to the known nonspiro substituted compounds.

SUMMARY OF THE INVENTION

The invention sought to be patented in its first composition aspect resides in the concept of a chemical compound of the formula:

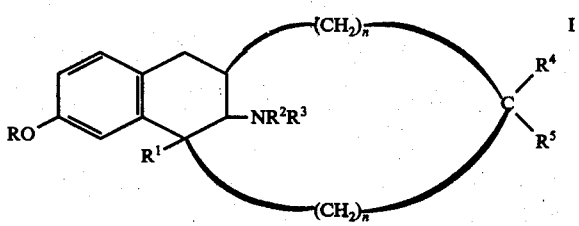

wherein R is hydrogen, lower alkyl, phen(lower)alkyl, substituted phen(lower)alkyl, lower alkanoyl, or carbocyclic aroyl; $R^1$ is lower alkyl of from 1 to 4 carbon atoms; $R^2$ and $R^3$ are independently selected from hydrogen, or lower alkyl of from 1 to 4 carbon atoms; $R^4$ and $R^5$ are independently selected from lower alkyl, or $R^4$ and $R^5$ may be concatenated to form a 5 or 6 membered carbocyclic ring; and n is 1 or 2; and the pharmaceutically acceptable addition salts thereof.

The tangible embodiments of the first composition aspect of the invention possess the inherent physical properties in the acid salt form of being crystalline solids, being substantially insoluble in non-polar solvents such as diethylether and soluble in polar solvents such as methanol and ethanol. Examination of compounds produced by the hereinafter described process reveals upon infrared and nuclear magnetic resonance spectrographic analysis, infrared and nuclear magnetic spectral data supporting the molecular structures herein set forth. The aforementioned physical characteristics taken together with the nature of the starting materials, the mode of synthesis and the elemental analysis, confirm the structures sought to be patented.

The tangible embodiments of the first composition aspect of the invention possess the inherent applied use characteristic of exerting analgesic effects in warm-blooded animals.

The invention sought to be patented in its second composition aspect resides in the concept of a chemical compound of the formula:

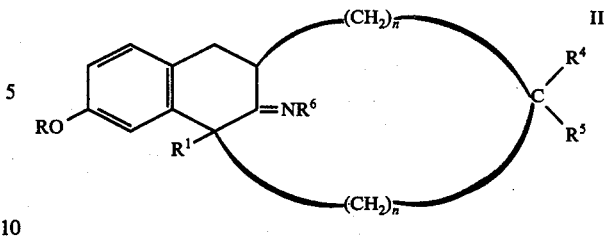

wherein R, $R^1$, $R^4$, $R^5$ and n are as defined hereinabove; and $R^6$ is hydrogen, hydroxy, (lower)alkoxy, phen(lower)alkoxy, or lower alkyl of from 1 to 4 carbon atoms.

The tangible embodiments of the second composition aspect of the invention possess the inherent physical characteristics of being substantially insoluble in water and being soluble in organic solvents such as lower alkanols, e.g. methanol, dilower alkyl ethers, e.g. diethyl ether, and hetero aromatics, e.g. pyridine.

Examination of compounds produced by the hereinafter described process reveals upon infrared and nuclear magnetic resonance spectrographic analysis, infrared and nuclear magnetic resonance spectral data supporting the molecular structures herein set forth. The aforementioned physical characteristics taken together with the nature of the starting materials and the mode of synthesis further confirm the structure of the compositions sought to be patented.

The tangible embodiments of the second composition aspect of the invention possess the inherent applied use characteristic of being intermediates in the synthesis of the compounds of Formula I.

The invention sought to be patented in its third composition aspect resides in the concept of a chemical compound of the formula:

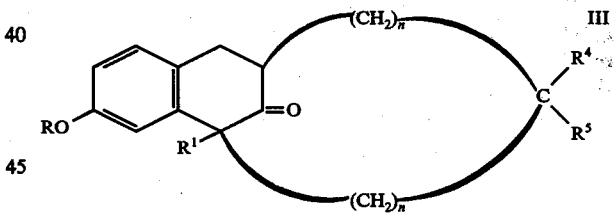

wherein R, $R^1$, $R^4$, $R^5$ and n are as defined hereinabove.

The tangible embodiments of their composition aspect of the invention possess the inherent physical properties of being substantially insoluble in water and being soluble in such organic solvents as lower alkanols, e.g. methanol; lower alkanones, e.g. acetone; and aromatics, e.g. benzene.

Examination of products produced by the hereinafter described process reveals upon infrared and nuclear magnetic resonance spectral analysis, infrared and nuclear magnetic resonance spectral data confirming the molecular structure herein set forth. The aforementioned physical characteristics taken together with the nature of the starting materials and the mode of synthesis further confirm the molecular structure herein set forth.

The tangible embodiments of the third composition aspect of the invention possess the inherent applied use characteristics of being intermediates in the synthesis of the compounds of Formula I.

The invention sought to be patented in its process aspect resides in the concept of a process for inducing analgesia in warm-blooded animals which comprises administering to a warmm-blooded animal in need thereof an effective amount of a compound of Formula I and a pharmaceutical carrier.

DESCRIPTION OF THE PREFERRED EMBODIMENT

To prepare the compounds of Formula III wherein R is lower alkyl, phen(lower)alkyl, lower alkanoyl, or carbocyclic aroyl; the correspondingly 7-substituted 1-lower alkyl-2-tetralone is treated, with a slight excess of 1 equivalent of base in an inert solvent, and then with an α,ω-dihalo-propane, or pentane bearing the desired spiro substitution in the 2 or 3 positions respectively. Treatment with a further slight excess over 1 equivalent of the strong base followed by work up using conventional techniques, gives the desired bridged tetralone product. The time and temperature are not especially critical, and for convenience the initial stages of the reaction are performed at room temperature during the course of 24 hours. The final stage of the reaction is conveniently run for a short period of time at slightly elevated temperature, conveniently usually the reflux temperature of the solvent employed, followed by a longer period at room temperature. Many suitable strong bases and solvents will occur to the skilled chemist, such as, for example, potassium t-butoxide in t-butanol or sodium hydride or sodium amide in dimethyl formamide. For example, 1-methyl-7-methoxy-2-tetralone is treated with a slight molar excess of freshly prepared potassium t-butoxide in tertiary butanol for a short period of time, conveniently one hour. This mixture is then added slowly to a solution of 1,1-bis-(β-bromoethyl)-cyclopentane in tertiary butanol and the mixture stirred for an extended period, conveniently about 18 hours. A second slight molar excess of potassium t-butoxide in tertiary butanol is then added, the solution is then warmed, conveniently to reflux, for a moderate period, conveniently about 6 hours, and is then allowed to stir for an additional extended period, conveniently about 18 hours, at the reaction temperature used for the remainder of the reaction, conveniently room temperature. Isolation of the product is conveniently accomplished by standard means. Partition between water and an immiscible organic solvent followed by evaporation of the solvent and vacuum distillation of the residue is one possible method. For example, the reaction mixture from the reaction between 1 methyl-7-methoxy-2-tetralone and 1,1-bis(β-bromoethyl)cyclopentane is poured into a large excess of water and extracted with an immiscible organic solvent, conveniently benzene, the solvent layers combined and evaporated to give a residue which is distilled under high vacuum to give 6',7',9',10',11',12'-hexahydro-3'-methoxy-5'-methylspiro[cyclopentane-1,3'(5'H)-[5,11]-methanobenzocyclodecen]-13'-one (IIIa). To prepare the compounds of Formula II, the compounds of Formula III are treated with hydroxylamine in a suitable solvent, conveniently hydroxylamine hydrochloride in pyridine, an alkoxyamine in a suitable solvent, for example methoxyaminehydrochloride in pyridine, a phen(lower)alkoxyamine in a suitable solvent, for example benzyloxyamine in methanol or benzyloxyamine hydrochloride in pyridine, ammonia or a primary amine of 1 to 4 carbon atoms in the presence of a water absorber for example anhydrous ammonia in the presence of Calcium oxide at elevated temperature conveniently 180°-190°. If the desired amine has a boiling point less than the desired reaction temperature or if anhydrous ammonia is used, the reaction is conveniently carried out in a pressure vessel. The oximino compounds are conveniently formed at room temperature. The isolation of these compounds may, if it is desired, be carried out by standard techniques. As an illustration, Compound IIIa is treated with excess hydroxylamine hydrochloride at elevated temperature, conveniently at reflux, and after removal of the solvent and partitioning of the residue between water and diethyl ether, 6',7',9',10',11',12'-hexahydro-3-methoxy-5'-methyl-spiro[cyclopentane-1,8'[5'H]-[5,11]methanobenzocyclodecen]-13'-one, oxime (IIa) is obtained as a crude oil of sufficient purity for further synthetic work. To prepare the compounds of Formula I, the compounds of Formula II are reduced, conveniently by hydrogenation in the presence of a suitable catalyst, but other methods will occur to a skilled organic chemist such as the use of a hydride reducing agent such as lithium aluminum hydride or a Bouveault Blanc type reduction, typically using sodium dissolved in a lower alkanol. A suitable hydrogenation method involves the use of hydrogen in the presence of Raney nickel and ammonia at 40-50 psi pressure. Isolation of the product is accomplished by standard techniques. A convenient method is conversion of the crude product obtained from the reaction mixture to an acid addition salt and then recrystallizing the salt. As an illustration, compound IIa is treated with hydrogen and Raney nickel in the presence of ammonia at 40-50 psi. After removal of catalyst and reaction solvent the crude product is converted to its crystalline hydrogen chloride addition salt and recrystallized to give 6',7',9',10',11',12'-hexahydro-3'-methoxy-5'-methylspiro[cyclopentane1,8'[5'H]-[5,11]methanobenzocyclodecen]-13'-amine The 1 lower alkyl-2-tetralones required for the practice of the invention may be prepared from the corresponding 1-unsubstituted 2-tetralone by a well-known alkylation reaction as typically described by Stork and Schulenberg in the Journal of the American Chemical Society, 84, 284 (1962). The tetralones are treated with pyrrolidine in an inert solvent such as benzene, and then reacted with the appropriate lower alkyl halide in an inert solvent such as benzene or dioxane, at elevated temperatures conveniently the reflux temperature of the solvent employed. They may also be prepared from a suitable 1-tetralone which may be treated, as described by Howell and Taylor in the Journal of the Chemical Society, 1958, 1249, with a Grignard reagent prepared from the appropriate lower halide, and the resulting 1-substituted dihydro-naphthalene oxidized with peracid.

Synthesis of tetralones which are not commercially available are readily available in the literature, e.g. the synthesis of α-tetralone is described in Organic Synthesis, Collective Volume IV, page 898, the synthesis of β-tetralone is described in the same work on page 903, and a general synthesis of β-tetralones is described in Nagata et al., Netherlands Pat. Nos. 6709534, Jan. 10, 1968.

The α,ω-dihalo propane or pentane bearing the desired substituent in the 2 or 3 positions respectively may be synthesized by methods described in *Journal of the American Chemical Society*, 74, 2885-2889, (1952); *Journal of the American Chemical Society*, 70, 946-949, (1948); *Journal of Organic Chemistry*, 29, 2637-2640, (1964); or *Journal of Heterocyclic Chemistry*, 2, 214–217, (1964).

It will be obvious to one skilled in the art of chemistry that the ketones of Formula III will be produced as racemic mixtures and that reduction of oximes or imines thereof will produce the amines of Formula I as diastereomers. The separation of the diastereomeric pairs and their resolution into enantiomers, if desired, may be accomplished by well-known procedures. The diastereomers, enantiomers, and mixtures thereof are all included within the scope of this invention.

The analgesic activity of the tangible embodiments of Formula I can be elicited by following a modification of the test procedure described by D'Amour and Smith in *Journal of Pharmacology*, 72, 74 (1941), an accepted test for analgesic agents. In this test, the compounds are administered intraperitoneally to rats, and the time required for response to a pain stimulus caused by a high intensity beam of light shining on the tail measured.

The compound of the invention exhibited analgesia when tested in this procedure exhibited activity at dosages greater than 10 mg. per kg. and particularly at doses of from 12.5 to 50 mg. per kg.

When the tangible embodiments of Formula I are employed as analgesic agents they may be administered to warm-blooded animals e.g. mice, rats, rabbits, monkeys and so forth, alone or in combination with pharmacologically acceptable carriers.

The dosage employed upon administration will vary with the form of administration and the compound chosen. Furthermore, it will vary with the particular subject under treatment. Generally treatment is initiated with small dosages substantially less than the optimum dose. Thereafter, the dose is increased in small increments until the optimum effect under the circumstances is reached. In general, the compounds of the invention are not desirably administered at a concentration level that will generally afford effective results without causing any harmful or deleterious side effects.

Except when limited otherwise by the context, as used herein and in the appended claims, the term "lower alkyl" means a saturated hydrocarbon radical, including the straight and branched radicals having from 1 to 6 carbon atoms, among which are, for the purposes of illustration, but without limiting the generality of the foregoing, methyl, propyl, and i-butyl. The term phen(lower) alkyl means a lower alkyl radical as hereinbefore defined, substituted in a terminal position by a phenyl radical among which are, for the purposes of illustration, but without limiting the generality of the foregoing, benzyl, phenethyl, and 2-methyl-2-phenylethyl. The term substituted phenyl (lower)alkyl means a lower alkyl radical as hereinbefore defined substituted in a terminal position by a phenyl radical substituted by lower alkyl or lower alkyloxy radicals, among which are, for the purposes of illustration, but without limiting the generality of the foregoing, o-, m-, or p-anisyl, veratryl, and o-, m-, or p-xylyl. The term "lower alkanoyl" means an aliphatic carboxyl radical, the hydrocarbon chain of which is a lower alkyl group as defined hereinabove, among which are, for the purposes of illustration but without limiting the generality of the foregoing acetyl, propionyl, or cyclopropane carboxyl. The term "carbocyclic aroyl" means a carbocyclic aromatic carboxyl group containing from 7 to 11 carbon atoms, among which are, for the purposes of illustration, but without limiting the generality of the foregoing benzoic, naphthoic, or p-, m-, or o-toluic.

The following examples illustrate the best mode contemplated by the inventors for the practice of their invention.

EXAMPLE 1

6',7',9',10',11',12'-Hexahydro-3'-Methoxy-5'-Methyl-spiro[Cyclopentane-1,3'(5'H)-[5,11]Methanobenzocyclodecen]13'-One Add a solution of 19 g. (0.1 m.) 1-methyl-7-methoxy-2-tetralone in 50 ml. dry tert butanol slowly to a freshly prepared solution of potassium tertiary butoxide. [4.6 g. (0.12 m.) potassium in 200 ml. tert butanol]. After addition is completed, stir the mixture for one hour. Transfer this solution under nitrogen into an addition funnel, and add the solution dropwise to a solution of 57 g. (0.2 m.) 1,1 bis($\beta$-bromethyl)cyclopentane in 150 ml. tert butanol. When addition is complete, stir the reaction at room temperature for 2 hours, add 2 g. potassium iodide, and allow to stir overnight.

The following day, add dropwise a freshly prepared batch of potassium tert butoxide [7 g. (0.12 m.) potassium in 200 ml. tert butanol]. Reflux the solution for six hours, and stir overnight at room temperature.

Pour the mixture into four liters of water, extract the product into benzene, and dry the benzene over magnesium sulfate. Remove the solvent on the rotary evaporator, and distill the residue, collecting the fraction from 205°–220° (at 0.8 mm. Hg., 22.4 g. — 71.8%.

EXAMPLE 2

5,6,7,8,9,10-Hexahydro-3-Methoxy-5,7,7-Trimethyl-5,9-Methanobenzocyclooctene-11-One By treating 1,3-dibromo-2,2-dimethyl propane and 1-methyl-7-methoxy-2-tetralone in the manner described in Example 1, one may prepare the title compound.

EXAMPLE 3

5,6,7,8,9,10,11,12-Octahydro-3-Methoxy-5,8,8-Trimethyl-5,11-Methanobenzocyclodecene-13-One By treating 1,5-dibromo-3,3-dimethylpentane and 1-methyl-7-methoxy-2-tetralone in the manner described in Example 1, one may prepare the title compound.

EXAMPLE 4

6',7',9',10',11',12'-Hexahydro-3-Methoxy-5'-Methyl-spiro[Cyclopentane-1,8'[5'H]-[5,11]Methanobenzocyclodecen]-13-One, Oxime The oxime is prepared by refluxing 16.2 g. (0.052 m.) of 6',7',9',10',11',12'-hexahydro-3-methoxy-5'-methyl-spiro[cyclopentane-1,8'[5H]-[5,11]methanobenzocyclodecen]-13-one in 650 ml. pyridine with a total of 96 g. hydroxylamine hydrochloride (25 g. hydroxylamine is added initially, then 10 g. portions are added twice each day) for a period of 4 days.

The pyridine is then recovered on the rotary evaporator, and the residue taken up in a mixture of water and ether. The ether layer is suspended, washed twice with water, and dried over $MgSO_4$. Removal of the ether gives 15.4 g. (90%) of a crude oil. Infrared and NMR spectra indicate that the product has the correct structure and is sufficiently pure to be used in the next step;

I. R.: 3335, 2900, 1640.

I. R. Analysis: $\lambda^{film}_{max}$ 3335, 2900, 1640 cm.$^{-1}$.

EXAMPLE 5

5,6,7,8,9,10-Hexahydro-3-Methoxy-5,7,7-Trimethyl-5,9-Methanobenzocyclooctene-11-One, Oxime By treating 5,6,7,8,9,10-hexahydro-3-methoxy-5,7,7-trimethyl-5,9-methanobenzocyclooctene-11-one with hydroxylamine hydrochloride in the manner described in Example 4, one may obtain the title compound.

EXAMPLE 6

5,6,7,8,9,10,11,12-Octahydro-3-Methoxy-5,8,8-Trimethyl-5,11-Methanobenzocyclodecene-13-One, Oxime By treating 5,6,7,8,9,10,11,12-octahydro-3-methoxy-5,8,8-trimethyl-5,11-methanobenzocyclodecene-13-one with hydroxylamine hydrochloride in the manner described by Example 4, one may obtain the title compound.

EXAMPLE 7

6',7',9',10',11',12'-Hexahydro-3'-Methoxy-5'-Methyl-spiro[Cyclopentane-1,8'(5'H)-[5,11]Methanobenzocyclodecen]-13'-Amine, Hydrochloride A mixture of 15.4 g. (0.047 m.) 6',7',9',10',11',12'-hexahydro-3-methoxy-5'-methylspiro[cyclopentane-1,8'[5H]-[5,11]-methanobenzocyclodecen]-13-one, oxime, 120 ml. absolute ethyl alcohol, 30 ml. concentrated ammonium hydroxide, and Raney nickel is hydrogenated on a Parr Hydrogenator for 5 hours. The catalyst is filtered off, and the solvent removed on a rotary evaporator. The crude oil (11.3 g.) is taken up in ether and dried over potassium carbonate. The drying agent is filtered off, and a hydrochloride salt formed by passing anhydrous hydrogen chloride gas through the ether solution. The crude hydrochloride salt (8.7 g.) is filtered off and recrystallized from methanol giving 3.4 g. (23%) pure hydrochloride salt of the title product, m.p. 324°–326°.

Analysis for: $C_{21}H_{31}NO.HCl$; Calculated: C, 72.08; H, 9.22; N, 4.00; Found: C, 71.86; H, 9.08; N, 3.72.

EXAMPLE 8

5,6,7,8,9,10-Hexahydro-3-Methoxy-5,7,7-Trimethyl-5,9-Methanobenzocyclooctene-11-Amine By treating the oxime of 5,6,7,8,9,10-hexahydro-3-methoxy-5,7,7-trimethyl-5,9-methanobenzocyclooctene-11-one with hydrogen in the presence of Raney nickel as described in Example 7, one may obtain the title product.

EXAMPLE 9

5,6,7,8,9,10,11,12-Octahydro-3-Methoxyl-5,8,8-Trimethyl-5,11-Methanobenzocyclodecene-13-Amine By treating the oxime of 5,6,7,8,9,10,11,12-octahydro-3-methoxyl-5,8,8-trimethyl-5,11-methano-benzocyclodecene-13-one with hydrogen and Raney nickel as described in Example 7, one may obtain the title product.

The subject matter which the applicants regard as their invention is particularly pointed out and distinctly claimed as follows:

1. A compound of the formula:

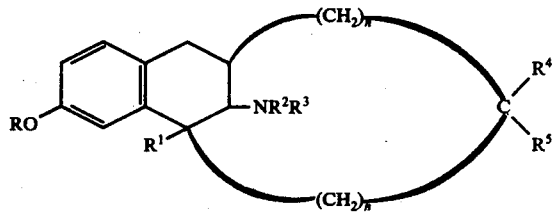

wherein R is lower alkanoyl; $R^1$ is lower alkyl of from 1 to 4 carbon atoms; $R^2$ and $R^3$ are independently selected from hydrogen, or lower alkyl of from 1 to 4 carbon atoms; $R^4$ and $R^5$ are independently selected from the group lower alkyl, or $R^4$ and $R^5$ may be concatenated to form a 5 or 6 membered carbocyclic ring; and n is 1 or 2 and the pharmaceutically acceptable addition salts thereof.

2. A compound as defined in claim 1 wherein n is 2.

* * * * *